US00PP36486P2

(12) United States Plant Patent
Clarkson

(10) Patent No.: US PP36,486 P2
(45) Date of Patent: Feb. 25, 2025

(54) ***FRAGARIA* PLANT NAMED 'DP64'**

(50) Latin Name: ***Fragaria* x *ananassa***
Varietal Denomination: DP64

(71) Applicant: Graham Clarkson, Faversham (GB)

(72) Inventor: Graham Clarkson, Faversham (GB)

(73) Assignee: EDWARD VINSON LTD., Faversham (GB)

( * ) Notice: Subject to any disclaimer, the term of this patent is extended or adjusted under 35 U.S.C. 154(b) by 0 days.

(21) Appl. No.: 18/807,649

(22) Filed: Aug. 16, 2024

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
CPC ..... A01H 6/7409; A01H 5/08
See application file for complete search history.

*Primary Examiner* — Keith O. Robinson
(74) *Attorney, Agent, or Firm* — Penny J. Aguirre

(57) ABSTRACT

A new and distinct everbearing *Fragaria* plant named 'DP64' that is characterized by its high fruit yields with a high proportion of marketable 'Class I' fruit, its fruit that is firm and has a very good post-harvest shelf life, its large plant size with strong vigor and a medium dense canopy, its dark leaves that exhibit medium blistering on the leaf surface and are predominantly convex in cross section, its fruit that is wide in relation to its length with a medium to strong glossy surface, and its fruit that is highly juicy with a moderate sugar content, and it is highly juicy with a moderate sugar content.

2 Drawing Sheets

Botanical classification: *Fragaria* x *ananassa.*
Variety denomination: 'DP64'.

BACKGROUND OF THE INVENTION

The present invention relates to a new and distinct cultivar of *Fragaria*, botanically known as *Fragaria* x *ananassa* 'DP64' and will be referred to hereafter by its cultivar name, 'DP64'. 'DP64' is an everbearing strawberry grown for fruit production.

The new cultivar was derived from an ongoing breeding program conducted by the Inventor at a farm in Faversham, Kent, The United Kingdom. 'DP64' arose from a controlled cross made by the Inventor in 2015 between unnamed and unpatented selections from the Inventor's breeding program; the female parent designated as accession number "EG34" and the male parent designated as accession number "CG36". 'DP64' was selected as a single unique plant in 2016 from amongst the seedlings that resulted from the above cross.

Asexual propagation of the new cultivar was first accomplished by rooting of stolons by the Inventor in Faversham, Kent, The United Kingdom in 2016. Asexual propagation by rooting of stolons and tissue culture using meristematic tissue has shown that the unique characteristics of the new cultivar are stable and reproduced true to type in successive generations.

BRIEF SUMMARY OF THE INVENTION

The following traits have been repeatedly observed and represent the characteristics of the new cultivar. These attributes in combination distinguish 'DP64' as a new and unique cultivar of *Fragaria.*

1. 'DP64' exhibits high fruit yields with a high proportion of marketable 'Class I' fruit.

2. 'DP64' exhibits fruit that is firm and has a very good post-harvest shelf life.
3. 'DP64' exhibits a large plant size with strong vigor and a medium dense canopy.
4. 'DP64' exhibits dark leaves that exhibit medium blistering on the leaf surface and are predominantly convex in cross section.
5. 'DP64' exhibits fruit that is wide in relation to its length with a medium to strong glossy surface.
6. 'DP64' exhibits fruit that is highly juicy with a moderate sugar content.

The female parent of 'DP64' differs from 'DP64' in having lower fruit yields and fruit that is paler in color with a lower acidity. The male parent of 'DP64' differs from 'DP64' in having fruit that is smaller in size, uneven in shape, and in being more susceptible to cracking on the fruit neck.

'DP64' can be most closely compared to the cultivar 'Eves Delight 2' (U.S. Plant Pat. No. 32,418). 'DP64' produces, on average, a greater total and percentage of class 1 fruit per plant than 'Eves Delight 2' and is larger in size with a higher average weight per berry across the growing season. The cropping seasons of the two varieties also differ, with 'Eves Delight 2' having an earlier profile than that of 'DP64'. Both plant habits can be described as semi-upright, although the plants of 'DP64' are generally larger, wider, and more spreading than 'Eves Delight 2'. The canopy of 'DP64' is also denser than that of 'Eves Delight 2'. On average, plants of 'DP64' produce more stolons than those of 'Eves Delight 2'.

The shape of the fruit is also different between the two varieties and represents one of the defining features of 'DP64'. 'DP64' expresses fruit that generally has a larger width in relation to its length, whereas with 'Eves Delight 2', the fruit has a larger length in relation to its width. For both varieties, the calyx is generally level with the surface of the fruit and roughly the same size as the diameter of the fruit. Because the fruit width of 'DP64' is on average larger than that of 'Eves Delight 2', the calyx of 'DP64' is also generally larger. The calyx on both varieties is strongly adhered to the fruit and are both mostly re-curved in relation to the fruit.

The color of the fruits can also be used to distinguish the two varieties. 'DP64' is a moderate red, whereas 'Eves Delight 2' fruit is usually paler in color. While both have glossy fruit surface appearances, the fruit of 'DP64' in general exhibits a higher level of gloss than that of 'Eves Delight 2'. The fruit of 'DP64' has a higher average number of achenes than 'Eves Delight 2'. The sugar levels in 'DP64' fruits are on average lower than those of 'Eves Delight 2'.

There are also differences in the leaf characteristics between the two varieties. Both the upper leaf surface color and the lower leaf surface color are a darker shade of green in 'DP64'. The leaf size and ratio of length to width is similar in the two varieties and the leaf margins are serrate to crenate. However, 'DP64' has slightly more serrations per leaf than 'Eves Delight 2'. The shape of the leaf in cross section also differs, with 'DP64' having a mostly convex aspect and 'Eves Delight 2' exhibiting a concave cross section.

While the petiole length is similar between 'Eves Delight 2' and 'DP64', the petiole thickness for 'DP64' is generally greater. The petioles have a weaker pubescence on the petioles in 'DP64' when compared to 'Eves Delight 2'. The petiolules appear to exhibit a similar thickness in both varieties, as well as a similar moderate pubescence. However, while the petiole length was similar in both varieties, the petiolule length is on average greater in 'Eves Delight 2'.

'DP64' generally starts flowering later than 'Eves Delight 2'. The flowers of 'DP64' are generally beneath the canopy, whereas the flowers of 'Eves Delight 2' are often observed to be level with the canopy. The peduncle length and thickness of each variety are similar, although differences arise in the pedicel whereby 'DP64' exhibits generally shorter pedicels that those of 'Eves Delight 2'. On average, 'DP64' has more flowers per truss than 'Eves Delight 2'.

The petal size also differs between the two varieties, with 'DP64' typically having smaller petals. Additionally, the petals of 'DP64' flowers are wider than they are long whereas for 'Eves Delight 2' the petals are rounder and are subsequently mostly equal in length and width. While the petal color is similar between 'DP64' and 'Eves Delight 2', the sepal color is generally paler in 'DP64' than it is in 'Eves Delight 2'. The Gynoecium is on average larger in 'Eves Delight 2' and while the anthers are similar in size, they do appear slightly larger in 'Eves Delight 2' than in 'DP64'.

BRIEF DESCRIPTION OF THE DRAWINGS

The accompanying color photographs illustrate the overall appearance and distinct characteristics of the new *Fragaria*. The photographs were taken of three-month-old plants (from a rooted plug) of 'DP64' as grown on tabletops in coir bags under tunnels with polyethylene covers in Faversham, Kent, The United Kingdom.

The photograph in FIG. 1 provides a close-up view of the berries of 'DP64'.

Figure 1:
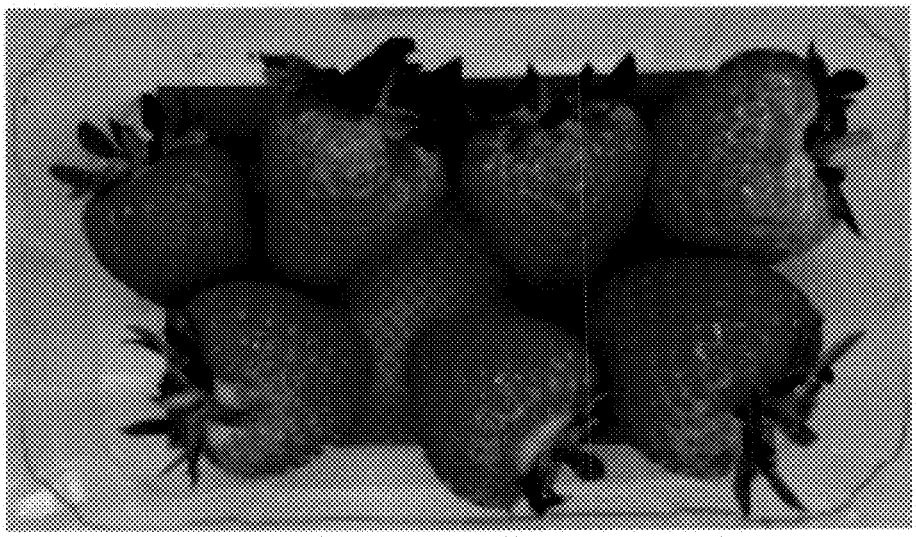
Figure 2:
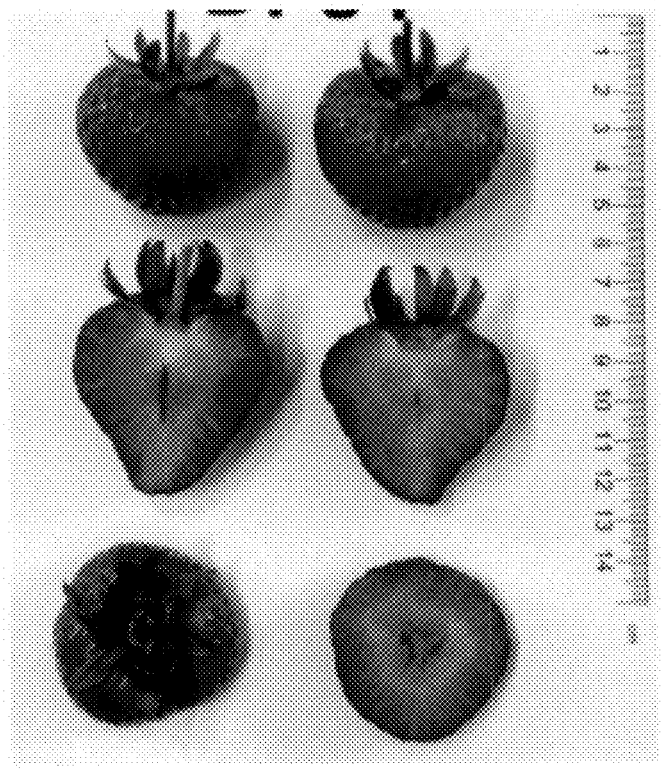

The photograph in FIG. 2. provides a close-up view of the berry flesh of 'DP64' cut both horizontally and vertically.

Figure 3:
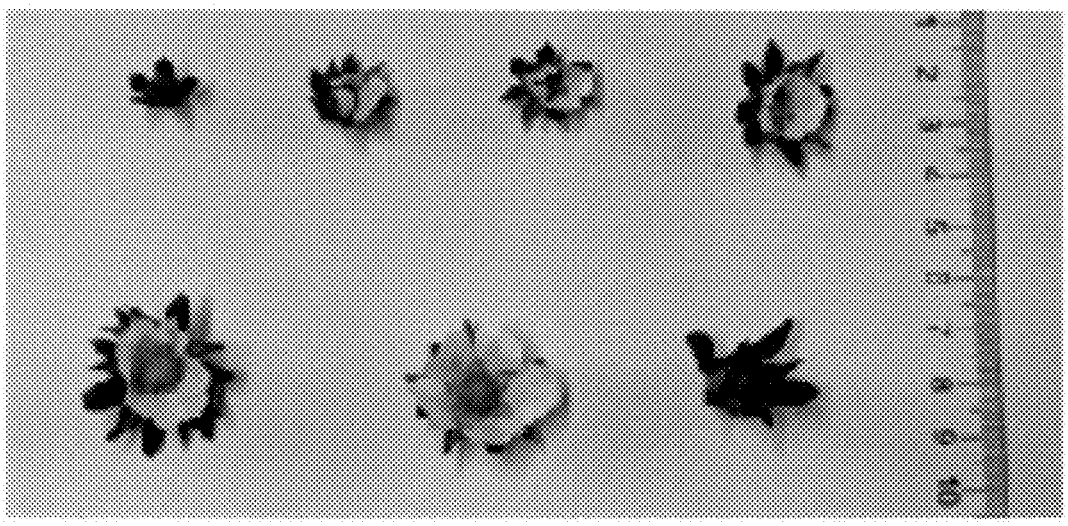

The photograph in FIG. 3 provides a close-up view of the different stages of development of the flowers of 'DP64'.

Figure 4:
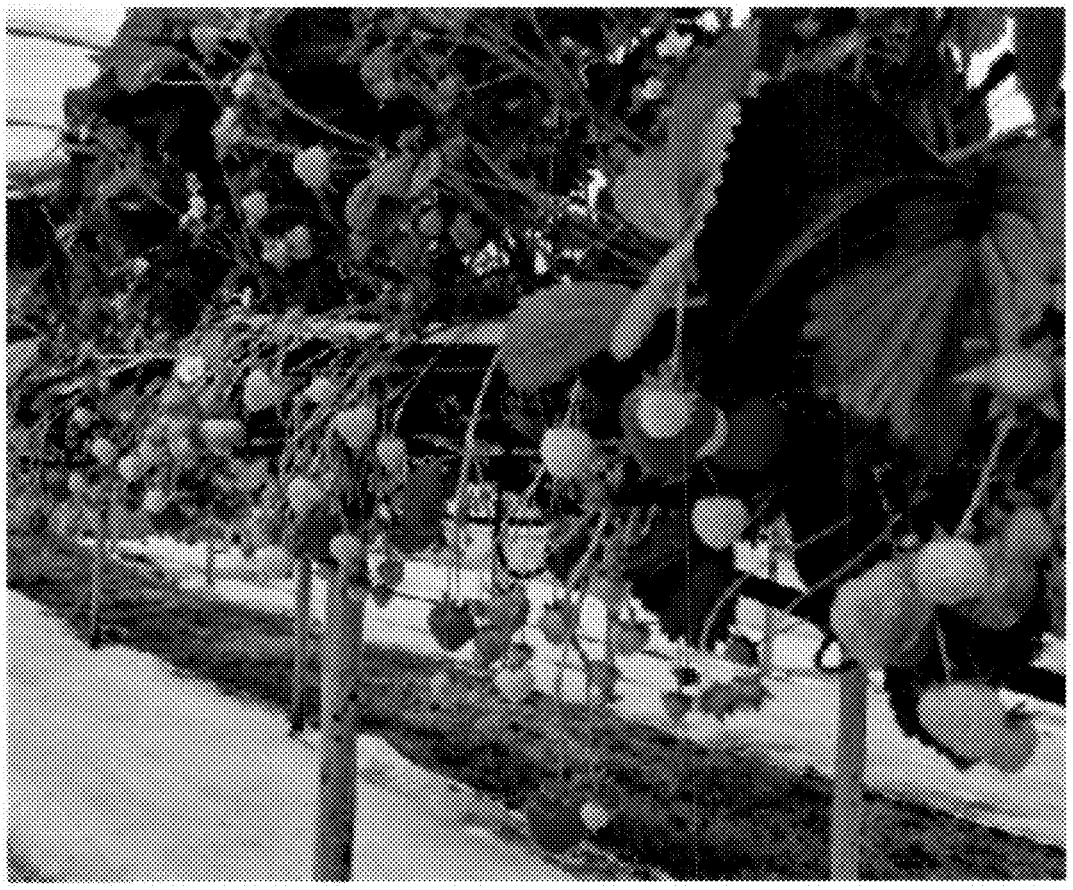

The photograph in FIG. 4 provides a view of the plant habit and display of fruit of 'DP64' in various stages of development.

The photographs depict color features as true as is reasonably possible with the digital photography methods used and the color values cited in the detailed botanical description accurately describe the new *Fragaria*.

DETAILED BOTANICAL DESCRIPTION

The following is a detailed description of three-month-old plants (from a rooted plug) of 'DP64' as grown on tabletops in coir bags under tunnels with polyethylene covers in Faversham, Kent, The United Kingdom. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Starting in April and continuing throughout the summer into autumn in Faversham, Kent, The United Kingdom.

*Plant type*.—Herbaceous fruit producing perennial.

*Plant habit*.—Semi-upright, medium dense canopy.

*Height and spread*.—Medium in size; reaches an average of 44.2 cm in height and 77.2 cm in width with an average height to width ratio of about 0.6:1 as a 3-month-old plant from a rooted plug.

*Crown*.—Average total diameter of 51 mm with an average crown number of 5.1.

*Cold hardiness*.—Not tested in areas where temperatures of less than 32° F. occur.

*Diseases and pests*.—Tolerance to *Botryotinia cinerea* (grey mold) and a slight susceptibility to *Podosphaera leucotricha* (powdery mildew) has been observed, no susceptibility or resistance to pests has been observed.

*Root description*.—Fibrous, NN155D in color.

*Root development*.—2 weeks to initiate roots, 5 weeks to produce a young rooted plant.

*Propagation*.—Rooting of stolons and tissue culture.

*Growth rate*.—Vigorous.

*Stem description*.—Acaulescent.

*Stolon description*.—144B with medium anthocyanin coloration of 173A.

Foliage description:

*Leaf division*.—Three leaflets.

*Leaf arrangement*.—Basal.

*Leaf attachment*.—Petiolate.

*Leaflet shape*.—Rounded.

*Mid-tier leaflet size*.—Average of 11.4 cm in length and 10 cm in width; an average length to width ratio of 1.1:1.

*Leaflet margins*.—Serrate to crenate with an average of 24 serrations per leaf.

*Leaflet base*.—Acute.

*Leaflet apex*.—Round.

*Leaflet glossiness*.—Medium.

*Leaflet aspect*.—Convex.

*Leaflet interveinal blistering*.—Medium.

*Leaflet venation*.—Pinnate, coloration matches leaflet color.

*Leaflet surface*.—Upper surface glabrous, lower surface very slightly pubescent, particularly along the vein.

*Leaflet color*.—Upper surface NN137A, lower surface N138B, no variegation present on either surface.

*Petiole*.—Round in shape, average of 26 cm in length and 5.4 mm in width, 146B in color, surfaces are sparsely pubescent with hairs held in a horizontal attitude.

*Petiolules*.—Round in shape, average of 1.7 cm in length and 2.7 mm in width, moderately pubescent surface, 144A in color.

*Stipule*.—Average of 2.3 cm in length and 1.1 cm in width, N34C in color.

Flower description:

*Inflorescence*.—Truss.

*Flower initiation and expression conditions*.—Temperature dependent.

*Time of flowering* (50% *of plants at first flower*).—Early-mid season.

*Number of flowers per truss*.—Average of 6.

*Flower position relative to foliage*.—Mostly held beneath the level of the leaf canopy.

*Flower size*.—Average of 2.4 cm in diameter and depth.

*Flower fragrance*.—Weak.

*Calyx*.—Average of 2.4 cm in diameter, same size as corolla.

*Sepals*.—Average of 10, oblanceolate in shape, obtuse base, acute apex, an average of 2.3 cm in length and 1 cm in width, color; 144B on both surface with the abaxial color early in the season 143B, truncate base, acuminate to acute apex, both surfaces pubescent, position; mixed arrangement relative to the fruit, most re-curving, some horizontal with fruit shoulder slightly inverted.

*Petals*.—Average of 5, average of 8.5 mm in length and 9.6 mm in width, round in shape, acute base, obtuse apex, touching to overlapping in arrangement, entire margins, upper and lower surface glabrous and N155B in color.

*Peduncle*.—144B in color, densely pubescent surface; hair attitude is upwards, strong in strength, average of 23 cm in length and 4 mm in width.

*Pedicel*.—N144A in color, moderately pubescent surface; hair attitude is upwards, strong in strength, average of 5.7 cm in length and 1.5 mm in diameter.

Reproductive organs:

*Gynoecium*.—Average of 4.8 mm in height and 4.7 mm in width, with a steeply dome shaped and slightly pointed top, multiple simple pistils present with capitate shaped stigma, stigma color 1A.

*Androecium*.—Stamens; average of 20, anthers; oval in shape, 1.1 mm in length, 0.7 mm in diameter, 13A in color, filament; 2.3 mm in length, 0.7 mm in diameter, and 154C in color, pollen; moderate in quantity, 2A in color.

Fruit description:

*Shape*.—Predominantly cordate to obloid, shape is similar for primary, secondary and tertiary fruit.

*Season of harvest*.—May through to End October in Faversham, Kent, The United Kingdom.

*Time of ripening* (50% *of plants with first ripe fruit*).—Early-mid season.

*Type of bearing*.—Everbearing.

*Size*.—Large; an average of 3.6 cm in length and 3.9 cm in width.

*Surface*.—Smooth, medium to highly glossy.

*Calyx position*.—Level with fruit to slightly indented.

*Attitude of calyx segments*.—Mostly re-curved with strong adherence to the fruit.

*Diameter of calyx relative to fruit diameter*.—Calyx is the same to size as the fruit diameter.

*Glossiness*.—Even and medium to strong.

*External color* (*skin*).—N34A, color is retained throughout the cropping season.

*Internal color* (*flesh*).—Near skin; 45A, near center; 44A.

*Evenness of color of skin*.—Very even.

*Evenness of color of flesh*.—Paler near center.

*Acidity*.—Low, total titratable acid an average of 0.6% over three seasons in trials.

*Sweetness*.—Medium.

*Soluble solids*.—Average of 8° over three seasons in trials.

*Firmness*.—Skin is firm (resistant to bruising), flesh is firm.

*Juiciness*.—High.

*Aroma*.—None.

*Weight*.—Average of 19 g per berry and 1,742 g per plant from late May to end of October over three seasons in trials.

*Hollow center*.—Slight on primary, secondary and tertiary fruit, more prominent on primary fruit, average of 6.6 mm in length and 2.7 mm in width.

*Shelf life*.—Very good, firm skin is resistant to bruising, with fruit color and gloss maintained up to and exceeding 7 days.

*Achene color*.—22A and 11A.

*Achene position*.—Majority below the surface.

*Achene number*.—An average of 303 per berry.

*Band within achenes*.—Absent to narrow.

*Fruit use*.—Primarily fresh fruit market.

It is claimed:

1. A new and distinct cultivar of *Fragaria* plant named 'DP64' as herein illustrated and described.

* * * * *